US010981849B1

(12) United States Patent
Wang et al.

(10) Patent No.: US 10,981,849 B1
(45) Date of Patent: Apr. 20, 2021

(54) METHOD FOR PREPARING CANNABINOIDS

(71) Applicant: SCI PHARMTECH INC, Taoyuan (TW)

(72) Inventors: Heng-Yen Wang, Taoyuan (TW); Feng-Hsu Li, Taoyuan (TW); Zhi-Jie Yang, Taoyuan (TW); Hsin-Yi Huang, Taoyuan (TW)

(73) Assignee: SCI PHARMTECH INC., Taoyuan (TW)

( * ) Notice: Subject to any disclaimer, the term of this patent is extended or adjusted under 35 U.S.C. 154(b) by 0 days.

(21) Appl. No.: 16/795,851

(22) Filed: Feb. 20, 2020

(51) Int. Cl.
*C07C 37/16* (2006.01)

(52) U.S. Cl.
CPC .................................. *C07C 37/16* (2013.01)

(58) Field of Classification Search
CPC .......... C07C 35/16; C07C 39/23; C07C 69/94; C07C 37/16; C07C 67/343; C07C 29/00; C07C 2601/16
See application file for complete search history.

(56) References Cited

U.S. PATENT DOCUMENTS

2007/0093665 A1\* 4/2007 Burdick .................. C07C 35/16
549/390

\* cited by examiner

*Primary Examiner* — Jafar F Parsa
(74) *Attorney, Agent, or Firm* — Kelly & Kelley, LLP

(57) ABSTRACT

Provided is a method for preparing synthetic cannabidiol, including hydrolysis-decarboxylation of a compound represented by formula (II) in a solvent-free state under atmospheric pressure. The method further includes preparation of the compound represented by formula (II). The method provides a safe, economical, environmentally friendly and scalable method for synthetic preparation of cannabidiol.

18 Claims, No Drawings

METHOD FOR PREPARING CANNABINOIDS

BACKGROUND

1. Technical Field

The present disclosure relates to methods for preparing cannabinoids, particularly to methods for preparing cannabidiol (CBD).

2. Description of Associated Art

Cannabidiol is a phytocannabinoid, one of the several cannabinoids identified in *cannabis* plants and accounts for up to 40% of the plant's extract.

It has been demonstrated to afford synthetic cannabidiol (CBD) via hydrolysis-decarboxylation of its corresponding intermediate, terpene-substituted olivetolate. One of the early examples of synthetic cannabidiol preparation via such process has been reported by Petrzilka, W. et al. in Helvetica Chimica Acta 52, 4, pp. 1102-1134 (1969) and shown in Scheme 1 below. In Scheme 1, Me refers to a methyl group; Et refers to an ethyl group; and aq refers to an aqueous solution.

Another early example of cannabidiol synthesis by hydrolysis-decarboxylation of olivetolate has been described by Gaoni in Tetrahedron 21, 5, pp. 1223-1229 (1965) and illustrated in scheme 2 below.

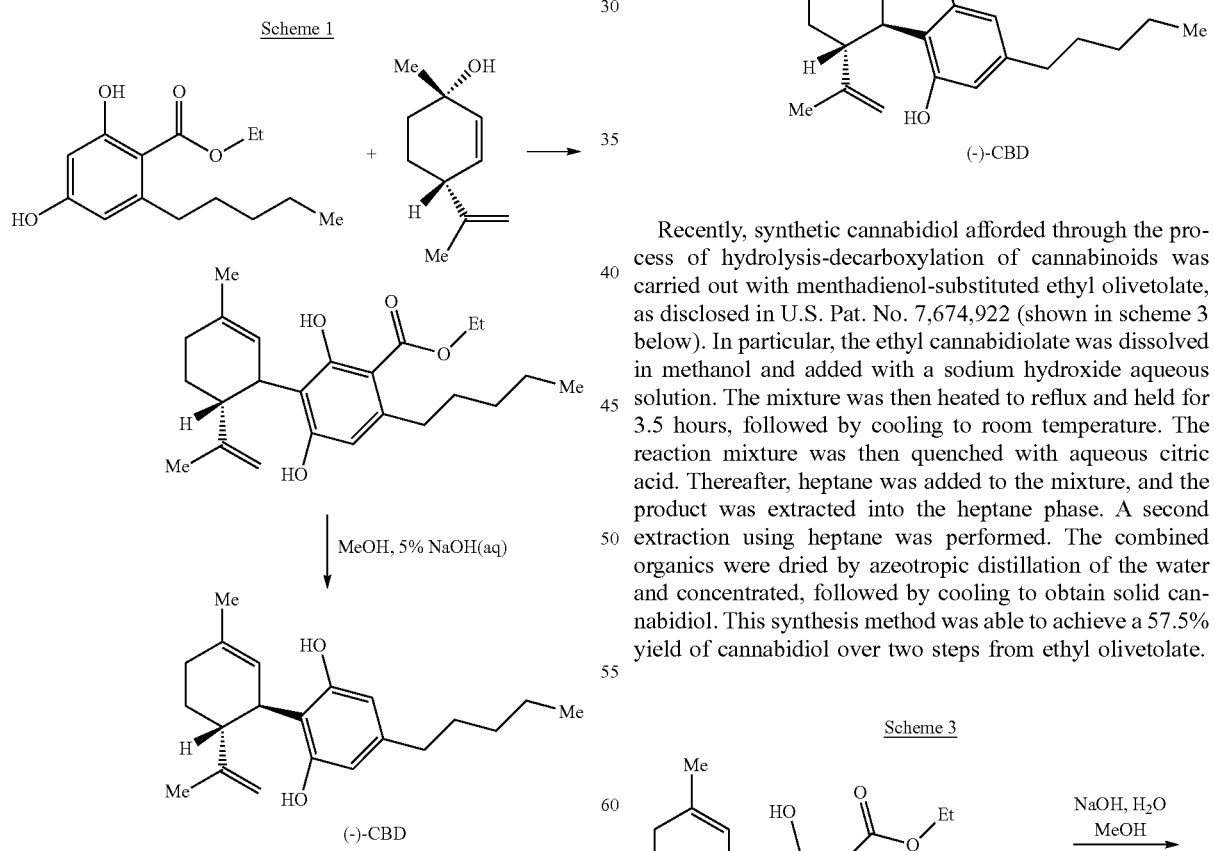

Recently, synthetic cannabidiol afforded through the process of hydrolysis-decarboxylation of cannabinoids was carried out with menthadienol-substituted ethyl olivetolate, as disclosed in U.S. Pat. No. 7,674,922 (shown in scheme 3 below). In particular, the ethyl cannabidiolate was dissolved in methanol and added with a sodium hydroxide aqueous solution. The mixture was then heated to reflux and held for 3.5 hours, followed by cooling to room temperature. The reaction mixture was then quenched with aqueous citric acid. Thereafter, heptane was added to the mixture, and the product was extracted into the heptane phase. A second extraction using heptane was performed. The combined organics were dried by azeotropic distillation of the water and concentrated, followed by cooling to obtain solid cannabidiol. This synthesis method was able to achieve a 57.5% yield of cannabidiol over two steps from ethyl olivetolate.

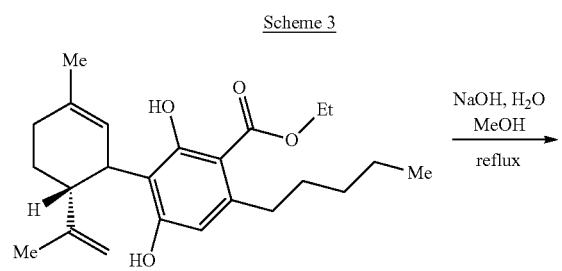

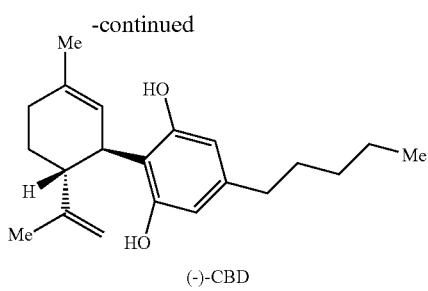

(-)-CBD

Moreover, European Patent No. 2,314,580 claimed to obtain a more than 95% reaction yield of hydrolysis-decarboxylation of menthadienol-substituted methyl olivetolate, by making use of a sealed reaction tank with a low boiling point solvent, such as MeOH (shown in scheme 4 below), or at atmosphere pressure with a high boiling point alcohol, such as ethylene glycol (shown in scheme 5 below).

Scheme 4

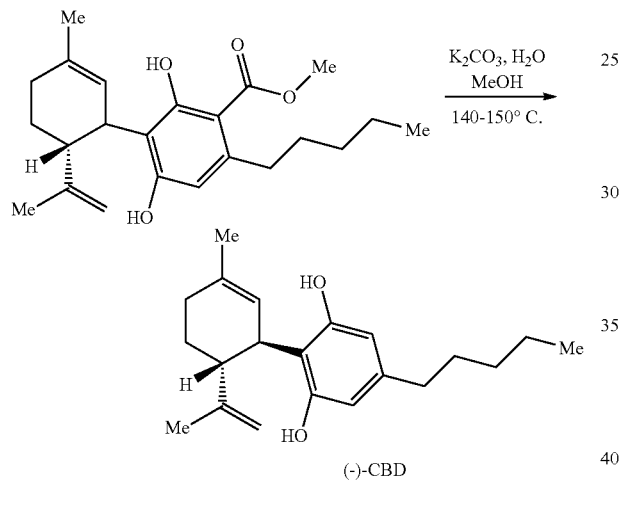

(-)-CBD

Scheme 5

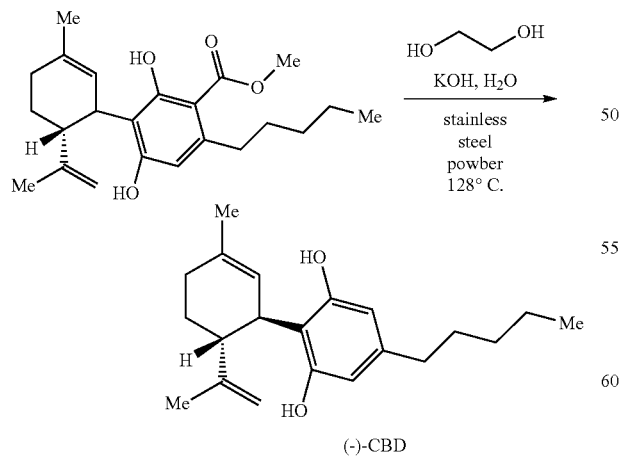

(-)-CBD

However, there were several concerns regarding the hydrolysis-decarboxylation method disclosed by European Patent No. 2,314,580 for industrial production. For example, the reaction was claimed to carry out in a low boiling point solvent under pressure and may pose significant safety hazard in bulk production. Specifically, combination of methanol and water was used as the solvent under the reaction temperature of 140° C. to 150° C. in a sealed reaction tank, which could produce a tremendous amount of methanol/water vapor in the sealed reaction tank and is hazardous in industrial scale production. In addition, the alternative method for the hydrolysis-decarboxylation reaction using high boiling point alcohol may require additional treatment to the aqueous organic waste after production. Further, using high boiling point alcohol may increase the risk of jeopardizing the quality of the cannabidiol product with a potential residual solvent, such as ethylene glycol, which is categorized as the Class II residual solvent in United States Pharmacopeia (USP) and should be avoided in pharmaceutical products.

Accordingly, there is still an unmet need in a safe, effective and environment-friendly method for the synthetic preparation of cannabidiol at industrial scale.

SUMMARY

In view of the foregoing, the present disclosure provides a method for preparing cannabidiol represented by formula (I) below,

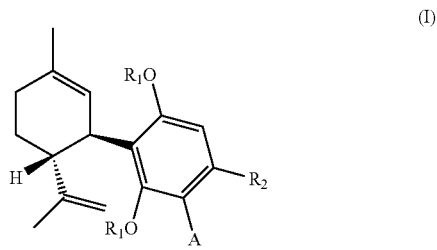

(I)

comprising hydrolysis-decarboxylation of a compound represented by formula (II) below,

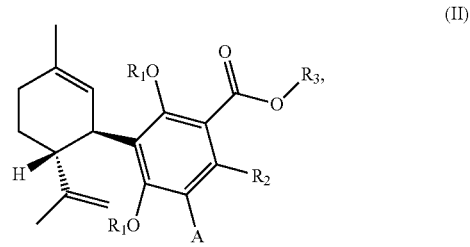

(II)

wherein $R_1$ is H, an alkyl group or a protecting group, $R_2$ is an-alkyl group or an ether group, $R_3$ is an alkyl group or a protecting group, and A is H or a carboxylic ester group.

DETAILED DESCRIPTION OF THE EMBODIMENTS

The following illustrative embodiments are provided to illustrate the disclosure of the present specification. These and other aspects and effects can be understood by those skilled in the art after reading the present disclosure. The present disclosure can also be performed or applied by other different embodiments. The details of the specification may be on the basis of different points and applications, and numerous modifications and variations can be devised without departing from the spirit of the present disclosure.

Prior to the present disclosure, alcohols, e.g., MeOH, are used as solvents in the hydrolysis-decarboxylation step of the cannabidiol synthesis. The present disclosure provides a method for preparing cannabidiol comprising hydrolysis-decarboxylation in an absence of a solvent. For example, the present disclosure provides a method for preparing cannabidiol comprising hydrolysis-decarboxylation without the use of alcohol. Such method provided in the present disclosure is environment-friendly, cost-effective and safe with good yield and quality.

The present disclosure provides a method for preparing cannabidiol represented by formula (I) below,

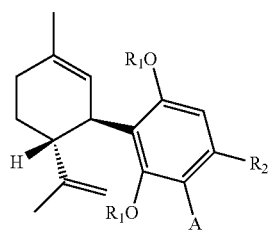

(I)

comprising hydrolysis-decarboxylation of an intermediate compound represented by formula (II) below,

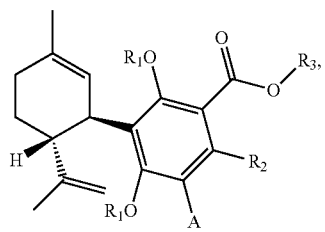

(II)

wherein $R_1$ is H, a $C_1$-$C_{16}$ alkyl group or a protecting group, $R_2$ is a $C_1$-$C_{16}$ group or an O—$C_1$-$C_{16}$ group, wherein $C_1$-$C_{16}$ is a straight or branched alkyl chain having one or more double or triple bonds at a position or having a substituent, such as a deuterium or halogen atom, phenyl, substituted phenyl, cycloalkyl, nitrile, alkoxy or a keto group, $R_3$ is a $C_1$-$C_{16}$ alkyl group or a protecting group, A is H or a COO—$C_1$-$C_5$ group, wherein $C_1$-$C_5$ is a straight or branched alkyl chain.

In an embodiment of the present disclosure, the protecting group may be a hydroxyl protecting group. In another embodiment, the hydroxyl protecting group is selected from the group consisting of tri-i-propylsilyloxymethyl (TOM), (phenyldimethylsilyl) methoxymethyl (SMOM), acetyl (Ac), pivaloyl (Piv), benzoate (Bz), trimethylsilyl (TMS), t-butyldimethylsilyl (TBDMS), triisopropylsilyl (TIPS), tri (trimethylsilyl)silyl (TTMSS), and t-butyldiphenylsilyl (TBDPS). In a further embodiment, the protecting group is represented by the formula O—$SiR_xR_yR_z$, wherein the substituents on the Si atom, namely $R_x$, $R_y$ and $R_z$, are required in order to satisfy the bonding orbital of the Si atom. The use of any particular substituent $R_x$, $R_y$ or $R_z$ is not especially limited. In an embodiment of the present disclosure, each of $R_x$, $R_y$ and $R_z$ is a $C_1$ or $C_2$ hydrocarbyl group (i.e., methyl or ethyl) simply because such materials are readily synthesized from commercially available materials.

In an embodiment of the present disclosure, the method further comprises preparation of the intermediate compound represented by formula (II), comprising: Lewis acid or Brønsted acid-promoted condensation of esterified olivetol represented by formula (III) below,

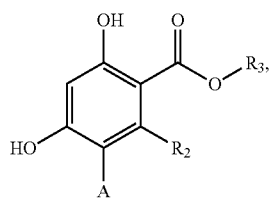

(III)

with terpene represented by formula (IV),

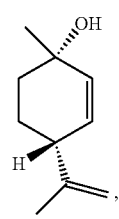

(IV)

wherein $R_2$, $R_3$ and A are described as above.

In an embodiment of the present disclosure, the method further comprises extraction of the intermediate compound represented by formula (II) with a solvent after Lewis acid or Brønsted acid-promoted condensation of esterified olivetol represented by formula (III). In a further embodiment, the solvent is an organic solvent. In another embodiment, the solvent is aprotic. In still another embodiment, the solvent is one with a low boiling point. In an embodiment, the solvent is a $C_5$-$C_7$ hydrocarbon that boils above 30° C. and below 100° C. In a further embodiment, the solvent is pentane, cyclopentane, hexane, cyclohexane, heptane, or a mixture thereof. In another embodiment, the solvent is hexane.

In an embodiment of the present disclosure, the method for preparing cannabidiol represented by formula (I) is illustrated by scheme 6 shown as follows:

Scheme 6

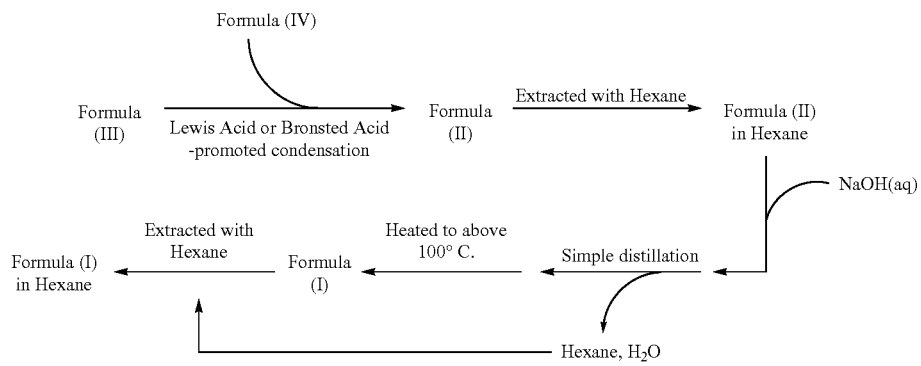

In the above scheme, simple distillation is carried out before the hydrolysis-decarboxylation of formula (II) to remove the organic solvent, hexane, and water to obtain neat formula (II). The distillate can be collected and reused for extraction of formula (I) prior to further purification. After distillation, the reaction is heated to above 100° C., and the neat formula (II) converts to formula (I) in a solvent-free state under atmospheric pressure.

In an embodiment of the present disclosure, formula (I) is prepared by hydrolysis-decarboxylation of formula (II) in absence of solvent. In a further embodiment of the present disclosure, formula (I) is prepared by hydrolysis-decarboxylation of formula (II) in an absence of alcohol. In an embodiment, the hydrolysis-decarboxylation of formula (II) is reacting in a neat state. In an embodiment, the hydrolysis-decarboxylation of formula (II) is reacting in a neat state by removing water and the solvent in the reaction. In a further embodiment, the water and solvent are removed from the reaction of hydrolysis-decarboxylation of formula (II) by simple distillation, such that the hydrolysis-decarboxylation of formula (II) is reacting in a neat state in absence of a solvent. In an embodiment, the hydrolysis-decarboxylation of formula (II) is reacting in a neat state in presence of base, e.g., a NaOH solution. In an embodiment, the hydrolysis-decarboxylation of formula (II) is carried out under atmospheric pressure.

In an embodiment of the present disclosure, the hydrolysis-decarboxylation of the intermediate compound represented by formula (II) is carried out above 100° C. In an embodiment of the present disclosure, the temperature is in a range from 101° C. to 130° C. In an embodiment of the present disclosure, the temperature is in a range from 105° C. to 125° C. In another embodiment of the present disclosure, the temperature to carry out hydrolysis-decarboxylation of the intermediate compound represented by formula (II) is 101° C., 102° C., 103° C., 104° C., 105° C., 106° C., 107° C., 108° C., 109° C., 110° C., 111° C., 112° C., 113° C., 114° C., 115° C., 116° C., 117° C., 118° C., 119° C., 120° C., 121° C., 122° C., 123° C., 124° C., 125° C., 126° C., 127° C., 128° C., 129° C., or 130° C.

In an embodiment of the present disclosure, the hydrolysis-decarboxylation of the intermediate compound represented by formula (II) is carried out in the presence of a base. In an embodiment, the base is a hydroxide of alkali metal. In an embodiment of the present disclosure, the base is NaOH or KOH.

In an embodiment of the present disclosure, the equivalent of the base is 3 to 5.

In an embodiment of the present disclosure, the base is NaOH, and the equivalent of NaOH is 3 to 5. In another embodiment of the present disclosure, the base is KOH, and the equivalent of KOH is 3 to 5.

In an embodiment of the present disclosure, condensation of formula (III) with formula (IV) is promoted by Lewis acid or Brønsted acid in presence of dichloromethane (DCM). In an embodiment of the present disclosure, the Lewis acid is boron trifluoride etherate, aluminium chloride, indium chloride, trimethylsilyl trifluoromethanesulfonate, stannic chloride, zinc chloride, zinc trifluoromethanesulfonate, ferric chloride, ferrous chloride, titanium chloride, scandium trimethylsilyl trifluoromethanesulfonate, or lanthanum trifluoromethanesulfonate. In another embodiment of the present disclosure, the Brønsted acid is p-toluenesulfonic acid or trifluoroacetic acid.

In an embodiment of the present disclosure, the Lewis acid is boron trifluoride etherate ($BF_3.OEt_2$).

The present disclosure provides a method for industrial production of cannabidiol that overcomes the defects of previously existing methods, for example, (a) saving the cost of raw material, alcohol, which is not required in the reaction; (b) saving the cost of processing alcohol waste; (c) economical and environmentally friendly by reusing the distillate; and (d) carrying out the hydrolysis-decarboxylation in a neat reaction under atmospheric pressure with no safety concern of the high pressure caused by the solvent during heating. Therefore, the present disclosure provides a method for cannabidiol synthesis that is safe and economical, and can be readily adopted in industrial scale operation in preference over the previously existing methods.

The following are examples further demonstrating the efficacy of the present disclosure, but are not to limit the scope of the present disclosure.

EXAMPLE

Example 1: Preparation of Formula (I) Via Ethyl Olivetolate (Formula III) with NaOH Through Hydrolysis-Decarboxylation Heated at 115° C. as a Neat Reaction Ethyl olivetolate (Formula III) (252 g, 1 mole) was diluted in dichloromethane, and the mixture was cooled to 0° C. followed by addition of $BF_3.Et_2O$ (28 g, 0.2 mole). Mixture of p-mentha-2,8-dien-1-ol (152 g, 1 mole) in dichloromethane was added into the ethyl olivetolate solution at 0° C., and the reaction mixture was stirred for one hour at 0° C. before quenched by 10% Na$_2$CO$_3$. The organic layer was subsequently collected and concentrated after phase separation, and the residue was diluted in hexane followed by washing with water twice to afford the crude compound of Formula II (301.3 g, 78.1 wt. % assayed by ultra-performance liquid chromatography (UPLC)).

The compound of Formula II in hexane (total weight 600 g) was subjected to conversion into the compound of Formula I without further purification. The crude compound of Formula II in hexane (120 g, 0.2 mole) was mixed with 20% NaOH(aq) (160 g, 0.8 mole) in a stainless reactor at ambient temperature. Simple distillation was carried out to remove hexane and water in the reaction mixture, and then heated at 115° C. for 2 hours to afford the crude compound of Formula I (44.1 g, 70.3 wt. % with a 2-step reaction from ethyl olivetolate assayed by UPLC).

Yield of hydrolysis-decarboxylation was calculated as 90.1% for the reaction carried out in this example.

Example 2: Preparation of Formula (I) Via Ethyl Olivetolate (Formula III) with NaOH Through Hydrolysis-Decarboxylation Heated at 125° C. as a Neat Reaction Ethyl olivetolate (Formula III) (252 g, 1 mole) was diluted in dichloromethane, and the mixture was cooled to 0° C. followed by addition of BF$_3$.Et$_2$O (28 g, 0.2 mole). Mixture of p-mentha-2,8-dien-1-ol (152 g, 1 mole) in dichloromethane was added into the ethyl olivetolate solution at 0° C., and the reaction mixture was stirred for one hour at 0° C. before quenched by 10% Na$_2$CO$_3$. The organic layer was subsequently collected and concentrated after phase separation, and the residue was diluted in hexane followed by washing with water twice to afford the crude compound of Formula II (301.3 g, 78.1 wt. % assayed by UPLC). The compound of Formula II in hexane (total weight 600 g) was subjected to conversion into compound (I) without further purification.

The crude compound of Formula II in hexane (120 g, 0.2 mole) was mixed with 20% NaOH(aq) (160 g, 0.8 mole) in a stainless reactor at ambient temperature. Simple distillation was carried out to remove hexane and water in the reaction mixture, and then heated at 125° C. for 2 hours to afford the crude compound of Formula I (42.4 g, 67.6 wt. % with a 2-step reaction from ethyl olivetolate assayed by UPLC).

Yield of hydrolysis-decarboxylation was calculated as 86.6% for the reaction carried out in this example.

Example 3: Preparation of Formula (I) Via Ethyl Olivetolate (Formula III) with NaOH Through Hydrolysis-Decarboxylation Heated at 105° C. as a Neat Reaction Ethyl olivetolate (Formula III) (252 g, 1 mole) was diluted in dichloromethane, and the mixture was cooled to 0° C. followed by addition of BF$_3$.Et$_2$O (28 g, 0.2 mole). Mixture of p-mentha-2,8-dien-1-ol (152 g, 1 mole) in dichloromethane was added into the ethyl olivetolate solution at 0° C., and the reaction mixture was stirred for one hour at 0° C. before quenched by 10% Na$_2$CO$_3$. The organic layer was subsequently collected and concentrated after phase separation, and the residue was diluted in hexane followed by washing with water twice to afford the crude compound of Formula II (301.3 g, 78.1 wt. % assayed by UPLC). The compound of Formula II in hexane (total weight 600 g) was subjected to conversion into the compound of Formula I without further purification.

The crude compound of Formula II in hexane (120 g, 0.2 mole) was mixed with 20% NaOH(aq) (160 g, 0.8 mole) in a stainless reactor at ambient temperature. Simple distillation was carried out to remove hexane and water in the reaction mixture, and then heated at 105° C. for 2 hours to afford the crude compound of Formula I (43.2 g, 68.8 wt. % with a 2-step reaction from ethyl olivetolate assayed by UPLC).

Yield of hydrolysis-decarboxylation was calculated as 88.2% for the reaction carried out in this example.

Example 4: Preparation of Formula (I) Via Ethyl Olivetolate (Formula III) with KOH Through Hydrolysis-Decarboxylation Heated at 115° C. as a Neat Reaction Ethyl olivetolate (Formula III) (252 g, 1 mole) was diluted in dichloromethane, and the mixture was cooled to 0° C. followed by addition of BF$_3$.Et$_2$O (28 g, 0.2 mole). Mixture of p-mentha-2,8-dien-1-ol (152 g, 1 mole) in dichloromethane was added into the ethyl olivetolate solution at 0° C., and the reaction mixture was stirred for one hour at 0° C. before quenched by 10% Na$_2$CO$_3$. The organic layer was subsequently collected and concentrated after phase separation, and the residue was diluted in hexane followed by washing with water twice to afford the crude compound of Formula II (301.3 g, 78.1 wt. % assayed by UPLC). The compound of Formula II in hexane (total weight 600 g) was subjected to conversion into the compound of Formula I without further purification.

The crude compound of Formula II in hexane (120 g, 0.2 mole) was mixed with 20% KOH(aq) (209 g, 0.8 mole) in a stainless reactor at ambient temperature. Simple distillation was carried out to remove hexane and water in the reaction mixture, and then heated at 115° C. for 1 hour to afford the crude compound of Formula I (42.0 g, 71.2 wt. % with a 2-step reaction from ethyl olivetolate assayed by UPLC).

Yield of hydrolysis-decarboxylation was calculated as 91.2% for the reaction carried out in this example.

Example 5: Preparation of Formula (I) Via Methyl Olivetolate (Formula III) with NaOH Through Hydrolysis-Decarboxylation Heated at 115° C. as a Neat Reaction Methyl olivetolate (Formula III) (47.6 g, 0.2 mole) was diluted in dichloromethane, and the mixture was cooled to 0° C. followed by addition of BF$_3$.Et$_2$O (6 g, 0.04 mole). Mixture of p-mentha-2,8-dien-1-ol (30.4 g, 0.2 mole) in dichloromethane was added into the methyl olivetolate solution at 0° C., and the reaction mixture was stirred for one hour at 0° C. before quenched by 10% Na$_2$CO$_3$. The organic layer was subsequently collected and concentrated after phase separation, and the residue was diluted in hexane followed by washing with water twice to afford the crude compound of Formula II (63.6 g, 85 wt. % assayed by UPLC). The compound of Formula II in hexane (total weight 208 g) was subjected to conversion to the compound of Formula I without further purification.

The crude compound of Formula II in hexane (63.6 g, 0.2 mole) was mixed with 20% NaOH(aq) (160 g, 0.8 mole) in a stainless reactor at ambient temperature. Simple distillation was carried out to remove hexane and water in the reaction mixture, and then heat at 115° C. for 1 hour to afford the crude compound of Formula I (39.8 g, 63.8 wt. % with a 2-step reaction from methyl olivetolate assayed by UPLC).

Yield of hydrolysis-decarboxylation was calculated as 75.1% for the reaction carried out in this example.

While some of the embodiments of the present disclosure have been described in detail above, it is, however, possible for those of ordinary skill in the art to make various modifications and changes to the particular embodiments shown without substantially departing from the teaching and advantages of the present disclosure. Such modifications and changes are encompassed in the spirit and scope of the present disclosure as set forth in the appended claims.

The invention claimed is:

1. A method for preparing cannabidiol represented by Formula (I),

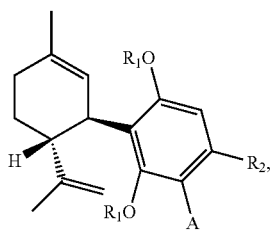
(I)

comprising hydrolysis-decarboxylation of a compound represented by Formula (II) in a solvent-free state at atmospheric pressure,

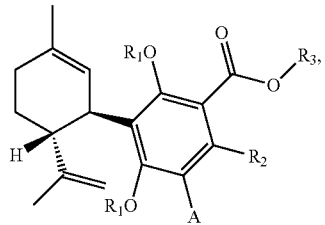
(II)

wherein $R_1$ is H, an alkyl group or a protecting group, $R_2$ is an alkyl group or an ether group, $R_3$ is an alkyl group or a protecting group, and A is H or a carboxylic ester group.

2. The method of claim 1, further comprising removing water and a solvent for the hydrolysis-decarboxylation to be carried out in the solvent-free state.

3. The method of claim 2, further comprising performing distillation to remove water and the solvent in the hydrolysis-decarboxylation.

4. The method of claim 2, wherein the solvent to be removed is $C_5$-$C_7$ hydrocarbon with a boiling point above 30° C. and below 100° C.

5. The method of claim 4, wherein the solvent is hexane.

6. The method of claim 1, further comprising heating at a temperature in a range from 101° C. to 130° C. in the hydrolysis-decarboxylation.

7. The method of claim 1, wherein the hydrolysis-decarboxylation is performed in a presence of a base.

8. The method of claim 7, wherein the base has an equivalent of from 3 to 5.

9. The method of claim 7, wherein the base is a hydroxide of an alkali metal.

10. The method of claim 9, wherein the base is KOH or NaOH.

11. The method of claim 1, further comprising preparing the compound represented by Formula (II) by Lewis acid or Brønsted acid-promoted condensation of a compound represented by Formula (III),

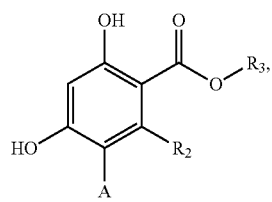
(III)

with a compound represented by Formula (IV),

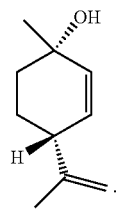
(IV)

12. The method of claim 11, wherein the Lewis acid is selected from the group consisting of boron trifluoride etherate, aluminium chloride, indium chloride, trimethylsilyl trifluoromethanesulfonate, stannic chloride, zinc chloride, zinc trifluoromethanesulfonate, ferric chloride, ferrous chloride, titanium chloride, scandium trimethylsilyl trifluoromethanesulfonate, and lanthanum trifluoromethanesulfonate.

13. The method of claim 12, wherein the Lewis acid is boron trifluoride etherate.

14. The method of claim 11, wherein the Brønsted acid is p-toluenesulfonic acid or trifluoroacetic acid.

15. The method of claim 11, wherein $R_1$ is H, $R_2$ is a $C_5$ alkyl group, $R_3$ is a $C_1$-$C_2$ alkyl group and A is H in the compound represented by Formula (III).

16. The method of claim 1, wherein $R_1$ is H, $R_2$ is a $C_5$ alkyl group and A is H in the compound represented by Formula (I).

17. The method of claim 1, wherein $R_1$ is H, $R_2$ is a $C_5$ alkyl group, $R_3$ is a $C_1$-$C_2$ alkyl group and A is H in the compound represented by Formula (II).

18. The method of claim 1, wherein the protecting group is selected from the group consisting of tri-i-propylsilyloxymethyl (TOM), (phenyldimethylsilyl)methoxymethyl (SMOM), acetyl (Ac), pivaloyl (Piv), benzoate (Bz), trimethylsilyl (TMS), t-butyldimethylsilyl (TBDMS), triisopropylsilyl (TIPS), tri(trimethylsilyl)silyl (TTMSS), and t-butyldiphenylsilyl (TBDPS).

* * * * *